Dec. 7, 1943. H. D. HAZARD ET AL Plant Pat. 610
WHITE FUCHSIA
Filed July 24, 1942
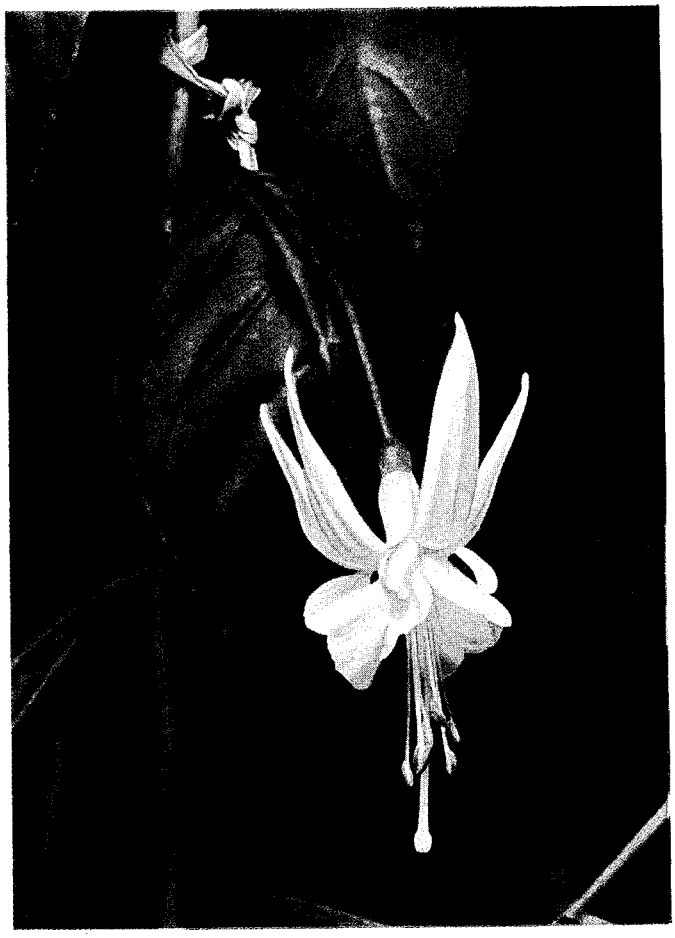
INVENTORS.
HUGH DODSON HAZARD
BESSIE ADELIA HAZARD
BY
Chas. E. Townsend
ATTORNEY.

Patented Dec. 7, 1943

Plant Pat. 610

UNITED STATES PATENT OFFICE

610

WHITE FUCHSIA

Hugh Dodson Hazard and Bessie Adelia Hazard, Monterey, Calif., assignors to George C. Roeding, Jr., Niles, Calif.

Application July 24, 1942, Serial No. 452,146

1 Claim. (Cl. 47—60)

This invention is the result of prolonged efforts, extending over a great many years, to produce a white fuchsia, not merely an albino but a beautiful white form that would combine much of the beauty and strength, vigor and other desirable qualities of the finest modern fuchsia, minus the weaknesses encountered in producing a white or albino.

In the course of our experiments, we have made many crosses. It was only after many attempts that we were rewarded with several fine "whites," the best of which we retained and which is the subject of the present invention.

It has size, form and rare beauty, all combining to give the flower great character. In addition, the plants are strong and free blooming.

We believe the new plant to be the largest and strongest nearly white fuchsia ever developed, as well as the most interesting of all modern fuchsias.

The accompanying colored photograph illustrates our discovery.

The following is a detail description of this new variety:

*Habit of growth:* Sturdy and bushy, either tall or low. It can be grown up to six feet in height, more or less, or as a basket fuchsia, all according to the requirements of and the skill of the grower. It is versatile, lending itself readily to many and various treatments.

*Buds:* White, long and streamlined.

*Flowers:* Medium to large in size, averaging about four inches across. A most beautiful white when not subjected to strong light. See also descriptions of tube, sepals and corolla.

*Foliage:* Healthy medium-green, nicely veined and of medium-size for the genus.

*Tube:* Short, about ⅜ inch to ½ inch; of good form and beautiful white, sometimes flushed with pink.

*Sepals:* Long, well-formed and of great substance; graceful and uniformly reflexed. Inside of a sparkling white, the texture of heavy crepe de chine; a beautiful white of waxy smoothness outside.

*Corolla:* Semi-full, with picoted petals. Petals variable in count (semi-full corolla).

*Stamens:* Firm, long and white, surmounted by anthers of glistening amaranth purple. (Ridgway P. XII.)

*Pistil:* White, strong, long-exserted. Stigma pink with pale yellow tip.

*Parentage*

The parentage of the white fuchsia reaches back well over a century to some of the fuchsias brought out by Dobbie, of Edinburgh.

We claim:

A new and distinct variety of white fuchsia plant, characterized by its size and strength, its long streamlined white buds, its flower having a short white tube sometimes flushed with pink, long well-formed sepals, with inside sparkling white and of waxy smoothness outside, long white stamens, and white pistil, substantially as shown and described.

HUGH DODSON HAZARD.
BESSIE ADELIA HAZARD.